United States Patent
Grundfest et al.

[11] Patent Number: 5,337,732
[45] Date of Patent: Aug. 16, 1994

[54] ROBOTIC ENDOSCOPY

[75] Inventors: Warren S. Grundfest, Los Angeles; Joel W. Burdick, IV; Andrew B. Slatkin, both of Pasadena, all of Calif.

[73] Assignee: Cedars-Sinai Medical Center, Los Angeles, Calif.

[21] Appl. No.: 945,806

[22] Filed: Sep. 16, 1992

[51] Int. Cl.$^5$ .............................................. A61B 1/00
[52] U.S. Cl. .............................................. 128/4; 604/95
[58] Field of Search ................... 128/4; 604/95, 97; 901/31, 39

[56] References Cited

U.S. PATENT DOCUMENTS

| | | |
|---|---|---|
| 2,855,934 | 10/1958 | Daughaday, Jr. |
| 3,279,460 | 10/1966 | Sheldon |
| 3,895,637 | 7/1975 | Choy ........................... 128/348 |
| 4,066,070 | 1/1978 | Utsugi ............................. 128/4 |
| 4,148,307 | 4/1979 | Utsugi ............................. 128/4 |
| 4,176,662 | 12/1979 | Frazer ............................. 128/6 |
| 4,207,872 | 6/1980 | Meiri et al. ..................... 128/4 |
| 4,389,208 | 6/1983 | LeVeen et al. ................ 604/95 |
| 4,447,227 | 5/1984 | Kotsanis ......................... 604/95 |
| 4,491,865 | 1/1985 | Danna et al. ............... 128/4 X |
| 4,577,621 | 3/1986 | Patel ............................. 128/4 |
| 4,653,476 | 3/1987 | Bonnet ........................... 128/4 |
| 4,676,228 | 6/1987 | Krasner et al. ................ 128/4 |
| 4,690,131 | 9/1987 | Lyddy, Jr. et al. ............. 128/4 |
| 4,706,655 | 11/1987 | Krauter ........................... 128/4 |
| 4,838,859 | 6/1989 | Strassmann ..................... 604/95 |
| 4,934,786 | 6/1990 | Krauter ........................ 350/96.26 |
| 5,018,509 | 5/1991 | Suzuki et al. ................. 128/6 |
| 5,196,017 | 3/1993 | Silva et al. ..................... 604/97 |

*Primary Examiner*—Richard J. Apley
*Assistant Examiner*—Beverly A. Meindl
*Attorney, Agent, or Firm*—Lyon & Lyon

[57] ABSTRACT

A robot for performing endoscopic procedures includes a plurality of segments attached to each other through an articulated joint. Actuators can move the segments together and apart and change their angular orientation to allow the robot to move in an inchworm or snake-like fashion through a cavity or lumen within a patient. Inflatable balloons around the segments inflate to brace a temporarily stationary segment against the lumen walls while other segments move. A compressed gas line attached to the back segment provides compressed gas to inflate the balloons and optionally to drive the actuators. The lead segment includes a television camera and biopsy arm or other sensors and surgical instruments.

18 Claims, 2 Drawing Sheets

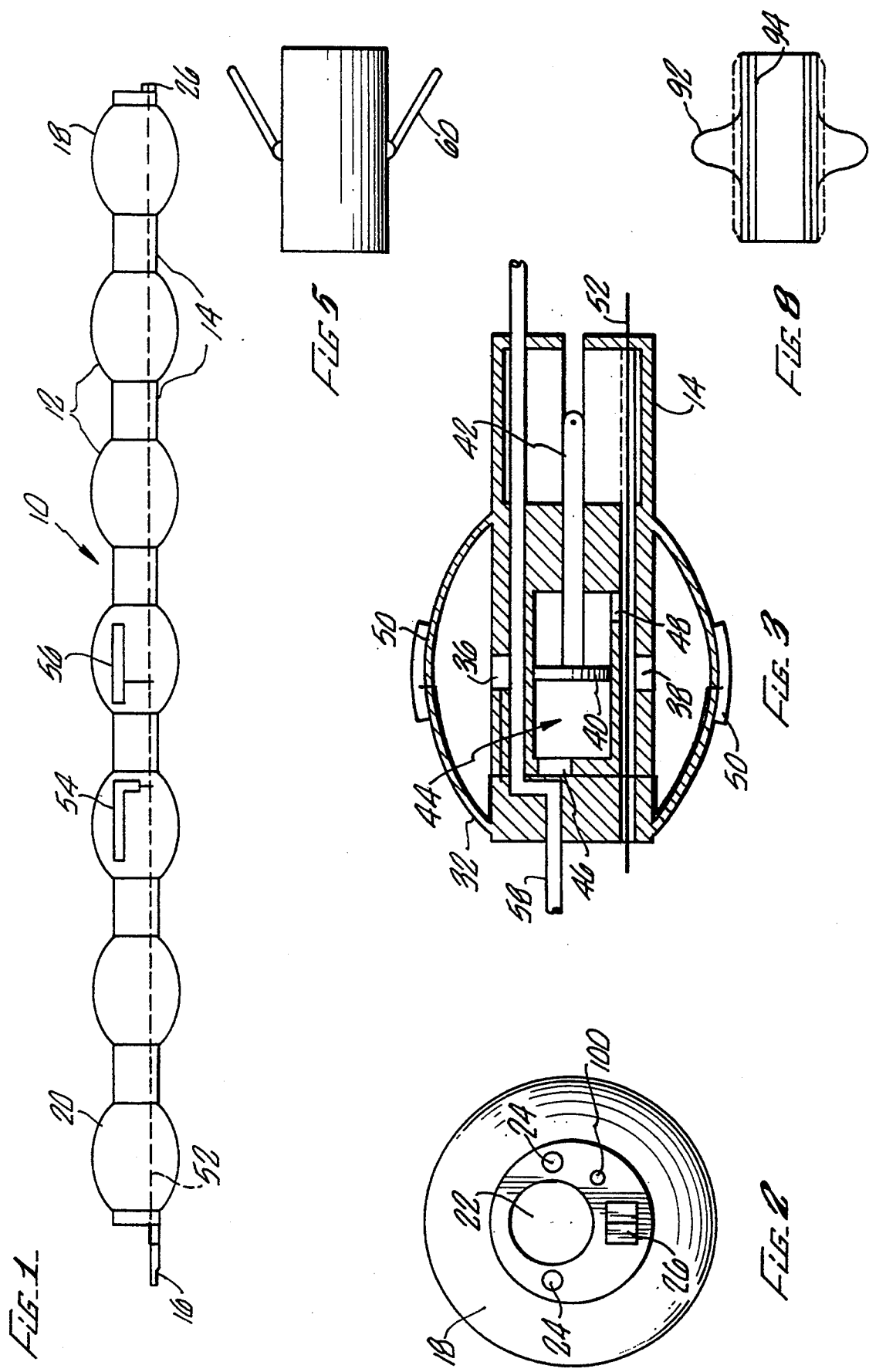

ROBOTIC ENDOSCOPY

BACKGROUND OF THE INVENTION

The field of the invention is endoscopy.

Minimally invasive medical techniques are aimed at reducing the amount of extraneous tissue which must be damaged during diagnostic or surgical procedures, thereby reducing patient recovery time, discomfort, and deleterious side effects. Arthroscopic knee surgery is the most widely known example.

A shift to minimally-invasive medical surgery is expected to be one of the biggest trends in medical practice in the 1990's. There are tremendous incentives for the medical community to adopt these techniques. Approximately 21,000,000 surgeries are now performed each year in the United States. It is estimated that 8,000,000 of these surgeries can potentially be performed in a minimally invasive manner. However, only about 1,000,000 surgeries currently use these techniques, due in part to limitations in minimally invasive surgical technology.

Advances in minimally invasive surgical technology could have a dramatic impact. The average length of a hospital stay for a standard surgery is 8 days, while the average length for the equivalent minimally invasive surgery in 4 days. Thus, the complete adoption of minimally invasive techniques could save 28,000,000 hospital days, and billions of dollars annually in hospital residency costs alone. Patient recovery times, patient discomfort, surgical side effects, and time away from work are also reduced with minimally invasive surgery.

Most current minimally invasive medical surgery and diagnostic techniques can generally be classified into two categories: laparoscopy and endoscopy.

A laparoscope is used for minimally-invasive inspection and surgery inside the abdominal cavity. Currently, laparoscopes are generally simple unarticulated tools which are inserted into the abdominal cavity via a hole in the abdominal wall. The laparoscope tip is mounted with simple surgical tools, such as scissors, clamps, tissue samplers, or cauterizers.

An endoscope is a highly flexible device for non-invasive inspection in interior cavities, canals (such as the colon), vessels, etc. Current endoscopes are comprised mainly of a fiber optic bundle for transmitting an optical image, and perhaps some simple mechanism for steering the tip of the endoscope. Their fiber optic bundles can also transmit laser beams which can cut, cauterize, or vaporize tissue. The term laparoendoscopic refers to the collection of these minimally invasive surgical techniques.

Endoscopic diagnoses and surgery is performed by inserting an endoscope into a natural or surgically induced orifice, and primarily traversing the colon, arteries, or other interior ducts. Endoscopes are more often used for inspection of interior cavities, though laser surgery is increasingly prevalent. For example, endoscopic lasers have been used to pulverize and remove kidney stones. While there have been some dramatic successes with laparoscopic and endoscopic surgery, the current state of the art in laparoscopic and endoscopic design technology, and function remains quite primitive.

There are a number of disadvantages with current laparoendoscopic technology. Commercial endoscopes, while highly flexible, have only limited steering ability. They are difficult to position and cannot traverse tight bends in the intestine (or other interior ducts, such as arteries). Consequently, about 60% of the gastrointestinal track is unreachable with current endoscope technology. As a result, many diagnostic and surgical procedures in the gastrointestinal track require large abdominal incisions. Further, sudden changes in the internal anatomical structure, such as stomach or colon cramping, are not easily accommodated with current endoscopes.

One of the biggest impediments to the expansion of minimally invasive medical practice is lack of access to interior cavities. In all types of current minimally invasive approaches, the diagnostic and surgical tools are long, thin devices which are inserted into naturally or surgically produced orifices. However, current devices are extremely limited in their mobility and ability make tight bends and to negotiate complex interior structures.

SUMMARY OF THE INVENTION

Hyper-redundant robots are a special class of kinematically redundant (or simply, redundant) robot manipulators which can have actively controlled geometries. Redundant robots posses more than the minimum number of degrees of freedom required to accomplish nominal tasks. Practically, redundant robots have seven or more internal degrees of freedom. Kinematic redundancy can improve robot versatility in complex environments, where the extra degrees of freedom can be used for obstacle avoidance, or to overcome deficiencies arising from kinematic, mechanical, and other design limitations inherent in non-redundant manipulators.

Hyper-Redundant robots have a very large degree of kinematic redundancy. These systems are analogous in morphology and operation to "snakes," "elephant trunks," "tentacles" or "earthworms". Because of their highly articulated structures, hyper-redundant robots are superior for applications and operation in very complicated and unusual environments.

The present invention is directed to a robot for performing endoscopic procedures. To this end, an endoscopic robot includes a plurality of segments articulated to each other. Actuators cause the segments to move together and apart, and to change the angular orientation between segments. Inflatable balloons around the segments provide traction for propulsion by engaging lumen or organ walls.

Accordingly, it is an object of the present invention to provide a hyper-redundant or snake-like robot for endoscopic procedures.

BRIEF DESCRIPTION OF THE DRAWINGS

Other objects and features of the present invention will become apparent from the following detailed description taken in connection with the accompanying drawings which disclose one embodiment of the invention. It is to be understood, however, that the drawings are designed for the purpose of illustration only and are not intended as a definition of the limits of the invention.

In the drawings, wherein similar reference characters denote similar elements throughout the several views:

FIG. 1 is a schematically illustrated side elevation view of the present endoscopic robot;

FIG. 2 is a front end view of thereof;

FIG. 3 is a partial section view of one segment of the robot of FIG. 1;

FIG. 5 is a schematically illustrated side elevation view of a segment with articulated arms;

FIG. 8 is a schematically illustrated side elevation view of another embodiment of a robot segment having bow wires.

DETAILED DESCRIPTION OF THE PREFERRED DRAWINGS

Figure 4:
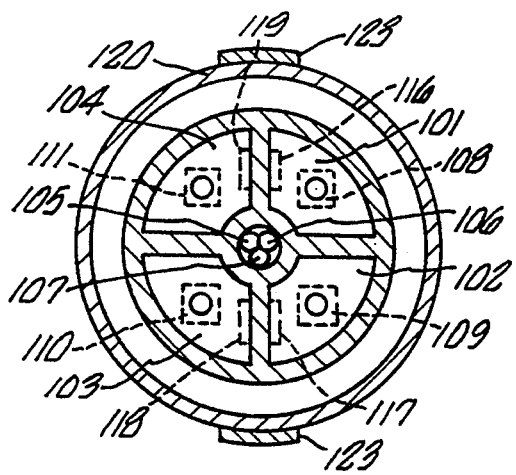
FIG. 4 is an end view of a segment of an alternative embodiment.

Turning in detail to the drawings, as shown in FIG. 1, an endoscopic robot 10 has a front or lead segment 18, a back segment 20, and a plurality of middle segments 12. Bellows 14 extend in between the segments. A compressed gas (e.g., $CO_2$ or air) supply hose 16 is attached to the back segment 20.

Referring to FIG. 2, the lead segment 18 includes a video camera 22, a pair of spaced apart lights 24 and a retracted biopsy tool with integral tissue storage cavity 26 and an insufflation port 100. Other surgical instruments may also be provided on the lead segment 18 including e.g., a laser, a needle or probe, etc.

Referring to FIGS. 1 and 3, an inflatable balloon 32 is attached around the outside of each segment. The balloon 32 is preferably toroidal. Within some or all of the segments is a cylinder 44 slidably containing a piston 40 having a joint link 42 extending to an adjacent segment. The joint is preferably either a pin or ball joint. A compressed gas line 58 linked to the supply hose 16 connects to an extend valve 46 and a retract valve 48 to control flow of a compressed gas into the cylinder 44 on either side of the piston 40. Valves 46 and 48 are individually controlled within each segment which has a piston and cylinder actuator. Similarly, pairs of inflation valves, e.g., 36 and 38 individually control flow of compressed gas from the compressed gas line 58 into each balloon 32 on each segment.

A control bus 52 extends through the robot 10 and is linked to the balloon inflation valves, as well as the valves 46 and 48 controlling movement of the piston 40. The bus 52 connects to a controller 54 and a receiver/transmitter 56. Tactile sensors 50 are provided on the inflatable balloons and are also linked to the bus 52. Other on-board microsensors, including PH sensors, or sensors for detecting enzymes, proteins or bacteria, or for measuring temperature of pressure may also be attached to the balloons.

In operation, the robot 10 is inserted into a body cavity or lumen such as the throat, upper or lower gastro-intestinal tracts, urinary track or biliary tract, either alone or with other endoscopic systems. The robot 10, moves forward through the lumen under its own power with an inchworm movement. The inchworm movement is achieved by temporarily bracing one or more segments against the lumen wall by selectively inflating some or all of the balloons 32, to prevent slippage, and by extending and contracting the segments together via the piston 40 and joint link 42 driven by compressed gas admitted into the cylinder 44 at appropriate times by the valves. The brace points in contact with the environment can be moved or adjusted as needed, while robot segments not in contact with the environment can be controlled to move the robot as desired. With multiple actuators between the segments, the robot can be controlled to propel itself or crawl through a lumen in either an inchworm mode, or in a concertina ( snake-like ) mode, to move forward or backward through the lumen. The concertina mode is especially useful where the diameter of the lumen exceeds the diameter of the fully expanded balloons on the segments. For example the diameter of the small and large intestines can vary by a factor of three along its length. Inch-worming motion suitable for the small diameter portion of the intestine will not work for the large diameter sections, where concertina motion is necessary. The robot 10 is controlled to fluidly transition from one locomotion scheme to another to adapt to the local changes in the environment.

The robot 10 may, for example, be delivered to the duodenum by a gastroscope. The robot 10 will then detach from the gastroscope and under its own propulsion system, move through the small intestine to a point of interest for diagnostic or laser surgery functions. The supply hose 16 trails behind the robot 10 to supply compressed gas as the driving medium. Using compressed air or gas to power the robot 10 is advantageous because compressed air is required for the endoscopy to insufflate or inflate the lumen ahead of the robot using insufflation port 100. In addition, air can be provided to the robot by a trailing hose which is fabricated from a dissolvable material, such as poly-glycolic acid derivatives. Once the robot has exited from the lumen, e.g., a gastrointestinal track, the air supply hose can be left inside the body, where it will dissolve within a day or two.

The controller 54 controls the valves for the cylinders and balloons using either predetermined sequences or as instructed by the surgeon and transmitted to the controller 54 via a transceiver outside of the patient's body through the transceiver 56 within the robot 10. Alternatively, the transceivers can be replaced with a trailing fiber-optic or metal wire control cable. Batteries within the robot 10 power the controller 54, transceiver 56 and the valves. The transceiver 56 can transmit images from the video camera 22 back to a monitor outside of the body through the transceiver 56. In an alternative embodiment, the piston 40 and cylinder 44 may be replaced with electrically driven actuators. A rear-looking imaging system, including ultrasound, may also be provided on the end segment 20.

The lead segment 18, with or without the biopsy arm 26 may also include devices to wash and dry the lens of the camera 22, irrigation capability, coagulation capability, optical spectroscopy, myographic recording, LIRS, as well as other probes or sensors. The biopsy tool can separately obtain biopsy samples from known and recorded locations and store them within the storage cavity 26 for testing after the robot 10 is removed from the patient. Correspondingly, a delivery arm on the robot can deposit or deliver drugs at a target location within the body.

In another application, one or more of the robots 10 may be used in a manner analogous to a "tugboat" to pull a fiber optic cable much deeper into the intestines than is currently possible with endoscopes. Once in position, the fiber can be used for laser based surgery.

As shown in FIG. 5, in an alternate embodiment, two or more articulated arms 60 extend from the robot segment. The arms 60 are driven (like oars) in a controlled sequence to propel the robot. Balloons may or may not be used with the segments having the arms 60.

Figure 6:
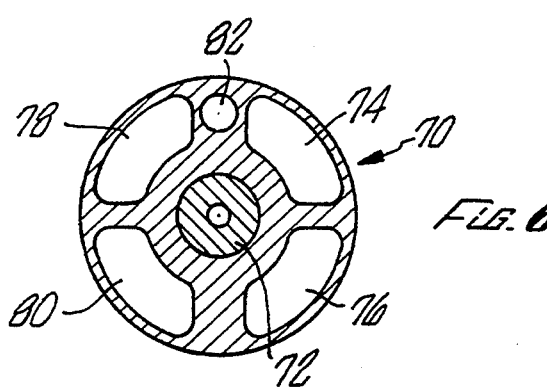
FIG. 6 is a partial section view of another embodiment of the present robot.

In another embodiment 70 shown in FIG. 6, a safety cable 72, of e.g., braided steel, Kevlar or carbon fibre extends centrally through the segments. Electrical power and control/communication lines 74, a gas supply line 76, a suction line 78, and an irrigation line 80 are spaced around the safety cable 72. A fibre optic cable 82 at the top of the robot delivers light to the front and/or back segments. In the event of a failure, the robot goes limp and can be withdrawn by pulling back on the safety cable.

Figure 7:
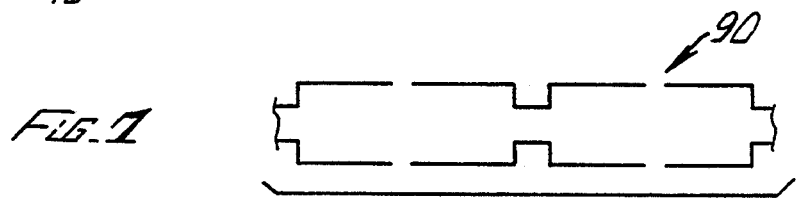
FIG. 7 is a side elevation view fragment of a sleeve component of the present robot.

FIG. 7 shows a cover or sleeve 90, preferably of plastic, which covers over and seals the robot segments. The sleeve 90 has openings for balloons or arms to extend through. The sections of the sleeve 90 between segments are highly flexible to allow the segments to freely move with respect to each other. The sleeve 90 may be removable, or a permanent part of the robot.

Figure 9:
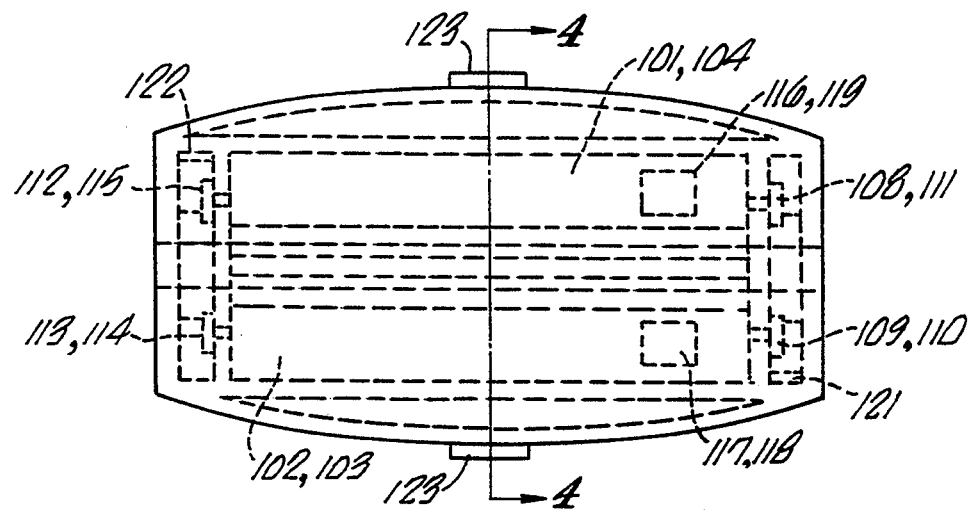
FIG. 9 is a side elevation view of the embodiment of FIG. 4.

As shown in FIGS. 4 and 9, an alternate embodiment of one robotic endoscope segment consists of four distinct inflatable sacs, 101, 102, 103, and 104. These sacs, which are comprised of an elastic material such as Latex, are circumferentially located around a central core. This core contains a high pressure compressed gas line 105, a low pressure or vacuum gas return line 106, and a control bus 107. Each sac is inflated or deflated by the action of valves 108–115. By controlling the relative pressure distribution in the sacs, using pressure sensors 116–119, the segment cannot only extend, as in the preferred embodiment, but also actively bend. This bending can be used to: actively control bending in parts of the intestine with tight radii or curvature and complicate shapes; position and orient the biopsy tool; implement concertina-like locomotion gaits; and assist in bracing of the robotic endoscope against the intestinal wall.

As in the previous embodiment, this alternate embodiment can also include a toroidal balloon 120 which is inflated or deflated by the action of valves 121 and 122. This balloon aids in the traction of the device by gripping the intestinal mucosa. This embodiment can also include tactile sensors 123 on the exterior of the segment to control the reaction forces between the balloon 120 and the intestinal wall. Of course, any number of sacs greater than or equal to three can be similarly used to effect the desired bending and extension of an individual segment.

FIG. 8 shows a segment embodiment having bow wires 92 which can be bowed outwardly by an actuator 94, to brace against a lumen wall. Segments may have two or more bow wires radially spaced apart.

The propulsion aspects of the present invention may also be applied to catheters or other tubular devices. For example, the propulsion elements shown in FIGS. 4 and 9 may be made part of or attached around a catheter. In addition, other devices having a series of segments, not necessarily only endoscopes, may include the present designs to achieve the propulsion described above.

Thus, although several embodiments have been shown and described, it would be obvious to those skilled in the art that many modifications to the present robot are possible, without departing from the spirit and scope of our invention.

What we claim is:

1. An endoscopic robot comprising:
    a plurality of segments, including a lead segment and an end segment;
    a plurality of pivoting joints each positioned in between and connecting adjacent segments;
    at least one actuator link extending through substantially through each pivoting joint and connecting to an adjacent segment;
    means for advancing and retracting the actuator links, to move the links together and apart for locomotion of the robot;
    an inflatable balloon supported around substantially each segment; and
    means for selectively inflating and deflating the balloons.

2. The robot of claim 1 further comprising an imaging device in the lead link.

3. The robot of claim 1 further comprising a single or multiple biopsy arm extendible from the lead link.

4. The robot of claim 1 wherein the means for controlling comprises microvalves opening into an air cylinder, and a controller linked to the microvalves by a bus.

5. The root of claim 1 further comprising a tactile sensor mounted on at least one of the inflatable balloons.

6. A substantially self-contained robot for performing endoscopic procedures, comprising:
    a plurality of segments pivotally attached to each other;
    a central core extending through the segments and containing gas supply and return lines and a control bus;
    a plurailty of inflatable sacs within each segment circumferentially positioned around the core and linked to the gas supply and return lines through sac valves;
    an inflatable balloon substantially surrounding the inflatable sacs of substantially each segment and linked to the gas supply and return lines through a balloon valve; and
    means for separately controlling the sac and balloon valves to inflate and deflate the sacs and balloon.

7. The robot of claim 6 further comprising a pressure sensor on the balloon and electrically linked to the bus.

8. The robot of claim 6 wherein the balloon is toroidal.

9. An endoscopy robot comprising:
    a plurality of segments attached to each other through an articulated joint, including a lead segment and an end segment;
    an actuator link extending through substantially each articulated joint and linking adjacent segments;
    a control bus extending through said segments;
    valves within each segment for individually controlling the actuator links;
    an inflatable balloon supported around substantially each segment; and
    means for selectively inflating and deflating the balloons, including at least one balloon inflation valve, located within each segment to be inflated and deflated.

10. The robot of claim 9 further comprising a controller located internal to said plurality of segments and linked through said control bus to said balloon inflation valves and to said valves for controlling said actuator link.

11. The robot of claim 9 further comprising a transceiver located internal to said plurality of segments and linked via said control bus to said controller.

12. The robot of claim 9 further comprising a trailing control cable attached to the end segment.

13. The robot of claim 9 further comprising a rear looking imaging section located in the end segment.

14. The robot of claim 9 further comprising a delivery arm externally attached to said lead segment.

15. The robot of claim 9 further comprising a pair of articulated arms on the lead segment.

16. The robot of claim 9 further comprising a safety cable extending through said segments.

17. The robot of claim 9 further comprising a flexible sleeve covering said segments and including clearance openings for the balloon.

18. The robot of claim 1 further comprising a flexible sleeve around the segments, the flexible sleeve including openings which allow the balloon to project through the sleeve.

* * * * *

UNITED STATES PATENT AND TRADEMARK OFFICE
CERTIFICATE OF CORRECTION

PATENT NO. : 5,337,732
DATED : August 16, 1994
INVENTOR(S) : Grundfest, et al.

It is certified that error appears in the above-indentified patent and that said Letters Patent is hereby corrected as shown below:

At Col. 1, in between lines 2 and 3, insert:
-- The U.S. Government has a paid-up license in this invention and the right in limited circumstances to require the patent owner to license others on reasonable terms as provided for by the terms of U.S. Navy Contract No. N00014-92-J-1920 awarded by the Office of Naval Research.--

At Col. 1, line 53, replace "is" with --are--.

At Col. 2, line 16, after "ability" insert --to--.

At Col. 2, line 33, replace "Hyper-Redundant" with --Hyper-redundant--.

At Col. 2, line 64, after "view" delete "of".

At Col. 5, line 32, replace "complicate" with --complicated--.

UNITED STATES PATENT AND TRADEMARK OFFICE
CERTIFICATE OF CORRECTION

PATENT NO. : 5,337,732

DATED : August 16, 1994

INVENTOR(S) : Grundfest, et al

It is certified that error appears in the above-indentified patent and that said Letters Patent is hereby corrected as shown below:

At Col. 6, line 30, replace "plurlaity" with --plurality--.

Signed and Sealed this

Seventeenth Day of October, 1995

Attest:

BRUCE LEHMAN

Attesting Officer

Commissioner of Patents and Trademarks